US005780675A

United States Patent [19]
Royer et al.

[11] Patent Number: 5,780,675
[45] Date of Patent: Jul. 14, 1998

[54] DEOXYGOSSYLIC COMPOUNDS

[75] Inventors: Robert D. Royer, Bosque Farms; Lorraine M. Deck; David L. VanderJagt, both of Albuquerque, all of N. Mex.

[73] Assignee: The University of New Mexico, Albuquerque, N. Mex.

[21] Appl. No.: 431,294

[22] Filed: Apr. 28, 1995

[51] Int. Cl.$^6$ .................................................. C07C 63/34
[52] U.S. Cl. .................. 562/467; 568/439; 568/440; 514/589; 514/700
[58] Field of Search ........................... 562/467; 568/439, 568/440; 514/589, 700

[56] References Cited

U.S. PATENT DOCUMENTS

| | | |
|---|---|---|
| 4,806,568 | 2/1989 | VanderJagt et al. |
| 5,026,726 | 6/1991 | VanderJagt et al. |

OTHER PUBLICATIONS

CA 121: 11825 (1993).
CA 122: 81663 (1994).
CA 76: 113018 (1971).
CA 122: 80802 (1994).
"Gossypol, A Pigment of Cottonseed", Adams et al, *Chem. Rev.* 60: 555–574, 1960.
"Biologically Active Derivatives of Gossypol: Synthesis and Antimalarial Activities of Peri–Acylated Gossylic Nitriles", R.E. Royer et al, *J. Med Chem* 26: 1799–1801 (1986).
"Inhibition of Human Immunodeficiency Virus Type I Replication by Derivatives of Gossylic", R.E. Royer et al, *Pharm. Res.* 24: 407–412 (1991).
"Efficient Synthesis of the Gossypol Binapthyl Backbone", M.C. Venuti, *J. Org. Chem* 46: 3124–3127 (1981).
"Synthesis of Apogossypol Hexamethyl Ether", J.D. Edwards, Jr. et al, *JACS* 79:, 2283–2285 (1957).
"Improved Synthesis of 1,2–Dimethoxy–3–Isopropylbenzene and General Synthesis of 3–Substituted–1, 2–Dimethoxy–benzenes", L.M. Deck et al, *Org. Prep. Proc. Int.* 22: 495–500 (1990).
"Orientation in Aromatic Substitution", J.D. Edwards, *JACS* 78: 3821–3824 (1956).
"A Conveninet Synthesis of the Important Retinoid Synthon Ethyl Trans–3–Formyl–2–Butenoate", R.W. Curley, Jr. et al, *Syn. Commun.* 16: 627–631 (1986).
"Factors Determining the Course and Mechanisms of Grignard Reactions", M.S. Kharasch et al, *JACS* 63: 2316–2320 (1941).
"Action du chlorure cobalteux anhydre, et du nitrate d'uranyl deshydrate sur quelques organomagnesiens et organolithiens aromatiques", Jean–Pierre Morizur, *Bull. Soc. Chim. Fr.:* 1331–1337 (1964).
"Synthesin aromatischer Aldehyde mit Dichlormethyl–alkylathern", A. Rieche et al, *Chem. Ber.* 93: 88–94 (1960).
"Total Synthesis of Insoflavones: Jamaicin, Calopogonium Isoflavone–B, Pseudobaptigenin, and Maxima Substance–B, Friedel–Crafts Acylation Reactions with Acid–ensitive Substrates", P.F. Schuda et al, *J. Org. Chem.* 52: 1972–1979 (1987).
"Selective Oxidation of Aldehydes to Carboxylic Acids with Sodium Chlorite–Hydrogen Peroxide", E. Dalcandale, et al, *J. Org. Chem.* 51: 567–569 (1986).
"The Cleavage of Ethers with Boron Bromide", F.L. Benton et al, *JACS* 64: 1128–1129 (1942).
"Oxidative Coupling . . . ", Belletire et al, *Tetrahedron Letters* 27: 127–130 (1986).
"Gossypol binds to a high–affinity binding site on human serum albumin", R.E. Royer et al, *FEBS Lett.* 157: 28–30 (1983).
"Development of a Sensitive Quantitative Focal Assay for Human Immumodeficiency Virus Infectivity", B. Chesebro et al, *J. Virol.* 62: 3779–3778 (1988).
"Binding of Gossypol Derivatives to Human Serum Albumin", R.E. Royer et al, *J. Pharm. Sci.* 77: 237–240 (1988).
"Polyphosphate as a Synthetic Agent . . .", Kanaoka et al, *Chem. Pharm. Bull.* 13: 1065–1072 (1965).

*Primary Examiner*—Paul J. Killos
*Attorney, Agent, or Firm*—Hoffman, Wasson & Gitler

[57] ABSTRACT

The invention provides deoxygossylic compounds having useful biological activities, and methods for the synthesis of these and related compounds. The invention further provides valuable intermediates for the synthesis of the compounds, and pharmaceutical compositions containing biologically active compounds according to the invention.

28 Claims, 1 Drawing Sheet

DEOXYGOSSYLIC COMPOUNDS

BACKGROUND OF THE INVENTION

The invention relates to novel gossylic compounds which retain clinical efficacies of gossypol and derivatives thereof, while exhibiting significantly lower toxicity.

1. Field of the Invention

Gossypol is a yellow pigment from the cotton plant of the formula:

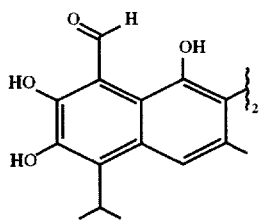

Gossypol has several potentially useful biological activities, including antiviral, antimalarial, antiparasitic, and contraceptive activity. Of particular interest is gossypol's recognized antiviral activity against enveloped viruses including HIV. Gossypol, however, is significantly cytotoxic at effective dosage levels for studied clinical applications, particularly antiviral activity, and the native compounds thus have had little clinical importance.

Gossypol toxicity has been associated with the 8,8'-dicarboxaldehyde groups, stimulating interest in derivatives or analogs in which the aldehyde groups have been derivatized to provide compounds which retain a substantial amount of the desirable biological activity of the parent compounds, while exhibiting decreased cytotoxicity.

2. Description of Related Art

Gossylic compounds wherein the aldehyde groups of gossypol have been modified in attempts to reduce toxicity of the parent compound have been prepared. However, the production of stable derivatives of gossypol in which only the aldehyde groups are modified has been limited because the sensitive phenolic hydroxyl groups in the 1,1' (peri) positions complicate the chemistry for modification of these groups (see, e.g., *Chem. Rev.* 60:555–574, 1960). On the theory that free peri hydroxyl groups might not be important for at least some of the biological activities of gossypol, including its anti-HIV activity, processes for derivatizing gossypol to block aldehyde functionality and reduce cytotoxicity have been developed wherein the peri hydroxyls are protected, or incorporated into the functional group replacing the aldehyde during synthesis. Such derivatizations of gossypol include the protection of the gossypol 1,1'-hydroxyl groups with acyl groups to provide gossylic nitriles as described in U.S. Pat. No. 4,806,568 to Vander Jagt et al.; the incorporation of the gossypol aldehyde groups into lactone or iminolactone functional groups which replace the aldehyde groups in gossylic (imino) lactones as described in U.S. Pat. No. 5,026,726 to Vander Jagt, et al.; and the derivatives described in *J. Med. Chem.* 26:1799–1801 (1986) and *Pharmacol. Res.* 24:407–412 (1991). Each of these references is incorporated herein by reference.

Some of these gossypol derivatives have proved biologically useful, particularly gossylic iminolactone (GIL), of the formula:

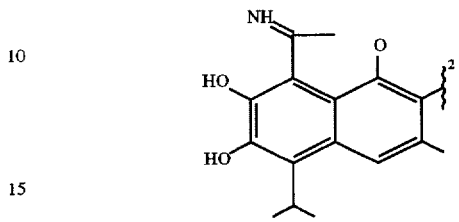

As a group, however, these derivatives do not provide the broadest range of functionality, as modified peri hydroxyl groups are always present. Further, processes for making hemigossypol derivatives using gossypol as a starting material are not believed to be known in the prior art. It is accordingly desirable to provide a de novo synthesis from simple precursors of gossypol analogs, including hemigossypol, which lack the gossypol peri hydroxyl groups.

BRIEF DESCRIPTION OF THE DRAWING

The sole FIGURE graphically illustrates anti-HIV activity of compounds according to the invention and gossylic iminolactone (GIL) as a function of percent foci reduction with increasing compound concentration. ◯=GIL; ●=BDG; ▼=DHG; ▽=BDGA; □=DHGA.

SUMMARY OF THE DISCLOSURE

Figure 1:
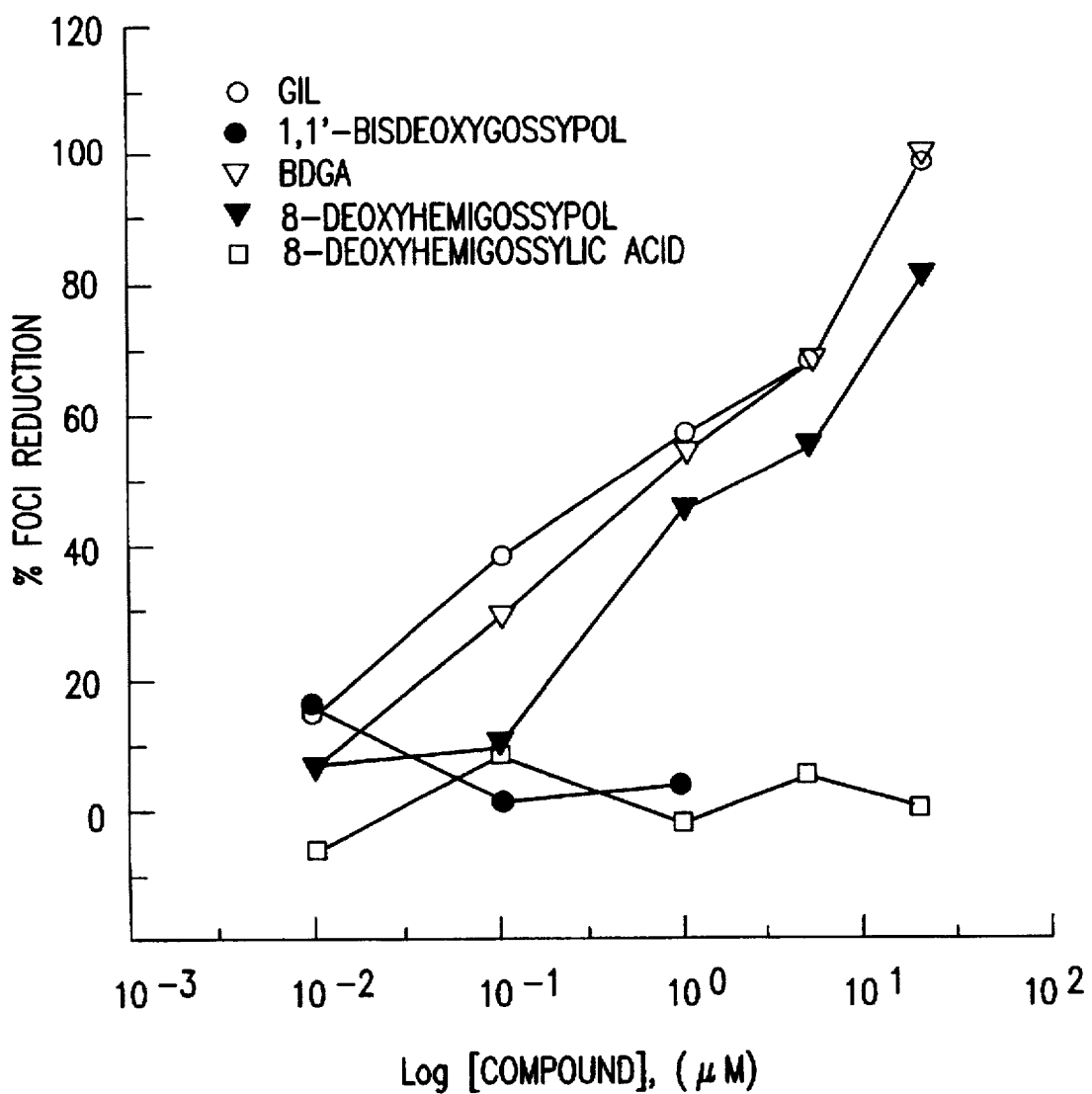

The invention comprises deoxygossylic and deoxyhemigossylic compounds of the formulas 3-6, below: 1,1'-bisdeoxygossypol (BDG, formula 3), 1,1'-bisdeoxygossylic acid (BDGA, formula 4), 8-deoxyhemigossypol (DHG, formula 5) and 8-deoxyhemigossylic acid (DHGA, formula 6). The compounds of the invention variously possess good biological activity, including antiviral activity, and reduced cytotoxicity, and/or are valuable intermediates for the production of useful gossylic compounds. The invention further comprises pharmaceutical compositions containing these compounds and syntheses for the production of these and gossylic compounds, including hemigossypols.

DETAILED DESCRIPTION OF THE INVENTION

Syntheses of the Compounds. Syntheses of compounds (3) and (4) are schematically illustrated in Scheme I. below. (Approaches to the synthesis of gossypol have also proceeded through tetralone 11 or similar structures, see, e.g., *J. Org. Chem.* 46:3124–3127, 1981; *J. Am. Chem. Soc.* 79:2283–2285, 1957.)

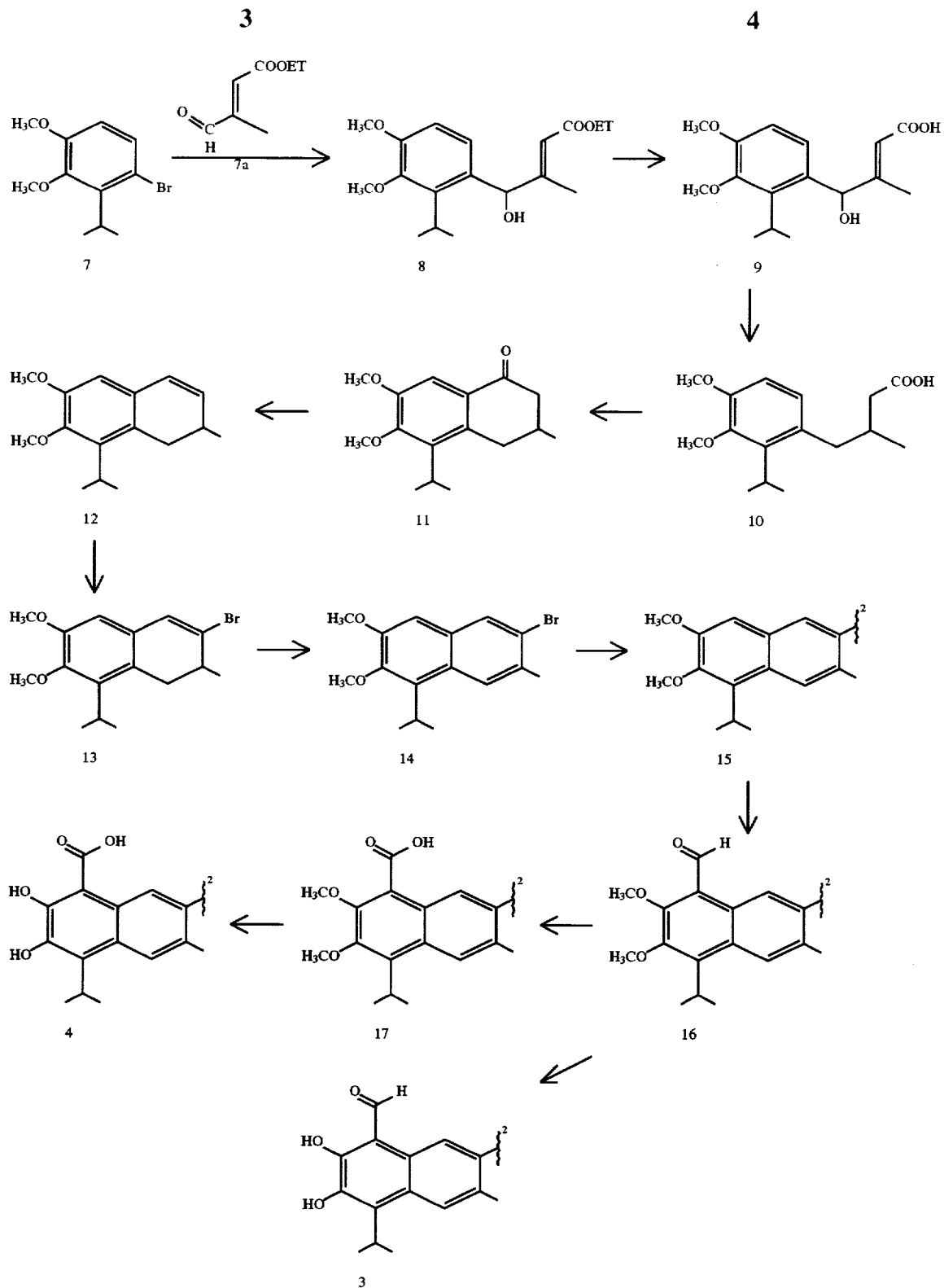

This synthesis features the incorporation of the carbon atoms for the second ring of the gossypol naphthalene system in one step by the reaction of the Grignard reagent from 1-bromo-2-isopropyl-3,4-dimethoxybenzene (7) with ethyl 3-methyl-4-oxobut-2-enoate (7 a) to form (8). These precursors are readily prepared from commercially available starting materials described in the literature (*Org. Prep. Proc. Int.* 22: 495–500, 1990; *J. Am. Chem. Soc.* 78:3821–3824, 1956; *Syn. Commun.* 16:627–631, 1986). The double bond of ester (8) is difficult to reduce in good yield so the ester is saponified to form the corresponding carboxylic acid (9) which is then catalytically hydrolyzed and reduced in one step. The resulting carboxylic acid (10) is cyclized with polyphosphoric ester according to *J. Org.*

Chem. op. cit. to form (11). The ketone function of (11) is reduced with sodium borohydride and the intermediate alcohol dehydrated on acidic workup to form (12). Compound (12) is treated with one equivalent of bromine in dichloromethand and a dibromide formed immediatels. This intermediate dibromide (uncharacterized herein) readily dehydrobrominated upon warming in DMF to form vinyl bromide (13). Compound (13) is aromatized by stirring with DDQ in benzene to form bromonaphthalene (14). The series of reactions used to convert (11) to (3) and (4) use simple procedures and generally proceed in good yield. The most challenging step is the coupling of two molecules of (14) to form (15). This is preferably accomplished by lithiating (14) with n-butyllithium and coupling with $CoCl_2$ catalyst, which provides a good yield (typically at least about 55% yield). (See, e.g., *J. Am. Chem. Soc.* 63:2316–2320, 1941 and *Bull. Soc. Chim. Fr.* 1331–1337, 1964). The functional groups on (16) are introduced by formylation of (15) with titanium tetrachloride and dichloromethyl methyl ether (see, e.g., *Chem. Ber.* 93:88–94, 1960 and *J. Org. Chem.* 52:1972–1979), and the aldehyde groups of (16) oxidized to carboxylic acids with sodium hypochlorite to form (17) (see, e.g.,*J. Org. Chem.* 51:567–569, 1986). The methyl groups are removed from the phenolic ethers (16) and (17) with boron tribromide to form (3) and (4), respectively (see, e.g., *J. Am. Chem. Soc.* 64:1128–1131, 1942 and *Tetrahedron Lett.* 27:127–130, 1986). These three transformations significantly reduce formation of by-products and are more efficient than other methods which were tried.

The syntheses of (5) and (6) are outlined in Scheme II, below. The transformations are accomplished by the same procedures used for the corresponding steps in Scheme I.

Antiviral activity has been demonstrated, and use of compounds of the invention as aldose reductase inhibitors for treatment of diabetics and lactate dehydrogenase inhibitors for antimalarial applications is also contemplated. Other compounds of the invention are valuable starting materials or intermediates for the production of biologically-active products of the invention, or other useful gossylic compounds. Extended descriptions of details for the in vivo, especially clinical, use of gossylic lactones and nitriles applicable to the practice of the present inventions directed to antiviral (especially HIV) and antimalarial clinical (including veterinary) use of the present compounds is found e.g., in the above-cited U.S. Pat. 4,806,568 and 5,026,726.

1. Anti-HIV Activity 1,1'-bisdeoxygossypol (BDG), 1,1'-bisdeoxygossylic acid (BDGA), 8-deoxyhemigossypol (DHG) and 8-deoxyhemigossylic acid (DHGA) were synthesized and tested for their ability to inhibit the replication of HIV in vitro. The $EC_{50}$ for BDGA was <1 µM and its threshold cytotoxicity was approximately 20 µM. BDG was less effective against HIV and much more cytotoxic than BDGA. DHGA was ineffective against HIV and showed very low cytotoxicity. DHG showed some anti-HIV activity, but the threshold cytotoxicity was at 5 µM. Inhibition of replication of H9/HIV-III$_B$ in HT46c cells by BDG, BDGA, DHG and DHGA is indicated in the FIGURE. GIL, previously shown to be more active and less cytotoxic than gossypol in similar assays (*Pharmacol. Res.*, op. cit.), was tested for comparison. Concentrations of compound which did not cause detectable changes in cell morphology or loss of monolayer adherence to the culture plate were considered to be below the threshold toxic concentration. Like BDGA, the $Ec_{50}$ for

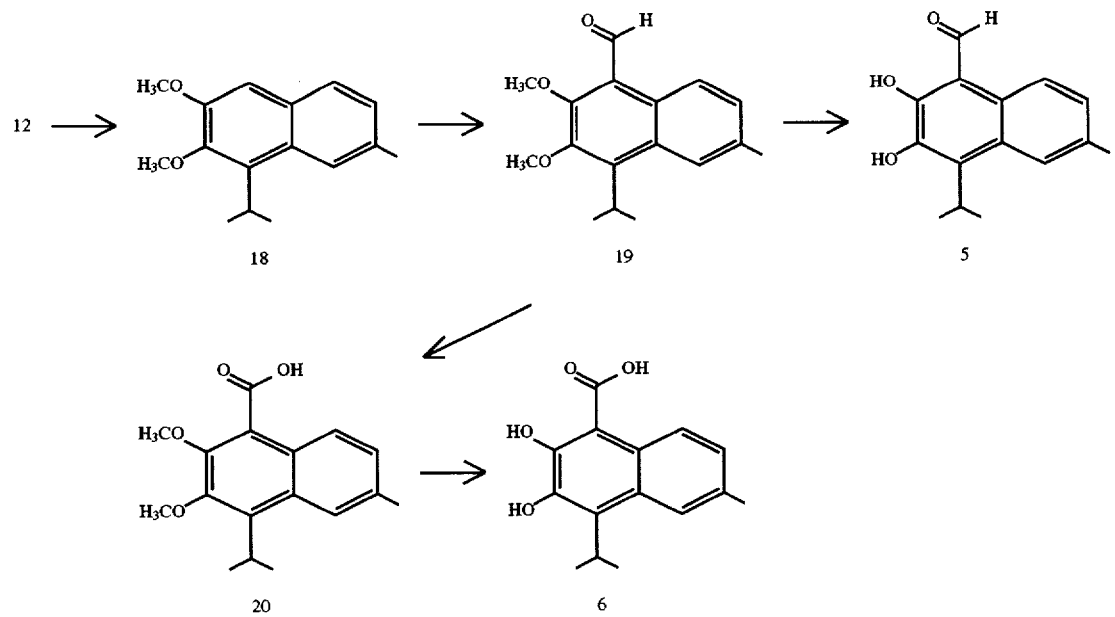

18   19   5

20   6

The references cited in the above section entitled "Syntheses of the Compounds" and in the below Examples are incorporated herein by reference.

Utility of the Compounds

Some of the compounds according to the invention retain biological activities exhibited by gossypol and several of its known derivatives, but have significantly lower cytotoxicity.

GIL was <1 µM. The same reduction in foci was obtained with GIL and BDGA at 5 µM. No toxicity was noted for GIL or BDGA at 5.0 µM. Some signs of monolayer destruction were observed with BDGA at 20 µM. BDG, on the other hand, was ineffective at 1 µM and destroyed >80% of the cell monolayer at 5 µM. DHGA had no observable effect on viral replication or cell morphology, even at 20 µM. DHG, on the other hand, did show some anti-HIV activity but was less active and more cytotoxic and GIL or BDGA.

GIL was previously found to be more effective than gossypol in inhibiting the replication of HIV in vitro. The present results show that BDGA is approximately as effective as GIL in vitro. Therefore, neither aldehyde groups nor 1,1'-hydroxyl groups are necessary for the anti-HIV activity of compounds related to gossypol. The results also show that the aldehyde groups in gossypol-related compounds are indeed responsible for much of their cytotoxicity.

2. Binding to Human Serum Albumin

Binding of gossypol-like compounds to serum albumin may reduce their free serum concentration, and therefore their effectiveness as a drug; this effect has been noted for gossypol and related compounds in in vitro experiments. The fluorescence quenching studies of binding of gossypol, GIL, BDG, BDGA, DHG, and DHGA described below demonstrate, however, that the small changes in the gossypol structure present in these compounds moderate the very tight binding of the molecule to the bilirubin binding site of serum albumin.

The dissociation constants for the binding of the six compounds to human serum albumin were determined by fluorescence quenching titrations; four were found to have much lower affinities for albumin than the parent compound, gossypol. Table I below lists the dissociation constants (Kds) for binding of compounds 1–6 to human serum albumin. The Kd for gossypol was determined by multiple methods as reported in *FEBS Lett.* 157:28–30, 1983. The Kds for compounds 2–6 were determined by fluorescence quenching titrations.

TABLE I

Dissociation constants (Kd) for the binding of gossypol-related compounds to human serum albumin.

| no. | compound | Kd (μM) |
| --- | --- | --- |
| 1 | gossypol | 0.09 |
| 2 | gossylic iminolactone | 3.0 |
| 3 | 1,1'-bisdeoxygossypol | 1.2 |
| 4 | 1,1'-bisdeoxygossylic acid | 1.5 |
| 5 | 8-deoxyhemigossypol | 0.66 |
| 6 | 8-deoxyhemigossylic acid | 5.28 |

EXAMPLES

Methods and Materials. Reagent quality solvents were used without further purification. THF and ether were dried over calcium hydride and filtered through scintered glass. The petroleum ether had bp 90°–100° C. Crystallizations were completed in a freezer at −15° C. The 1-bromo-2-isopropyl-3,4-dimethoxybenzene (7) was synthesized by brominating 1,2-dimethoxy-3-isopropylbenzene (*Org. Prep. Proc. Int.* op. cit.) according to a published procedure (*JACS* 78:3821–3824, 1956) at −5° to 0° C. Melting points were determined with a VWR Scientific Electrothermal capillary melting point apparatus and are uncorrected. IR spectra were recorded on a Beckman model IR-33 spectrometer in KBr pellets. NMR spectra were recorded on a Bruker AC250 NMR spectrometer in $CDCl_3$. Chemical shifts are in δ units relative to TMS. Signals for isopropyl methyl groups are reported as doublets, although, at 25° C. some show slight additional splitting due to rotational isomers.

Example I. Chemical Synthesis

Ethyl 4-Hydroxy-4-|3,4-dimethoxy-2-(1-methylethyl) phenyl|-3-methylbut-2-enoate (8). Compound 7 (10.0 g, 38.6 mmol) and ethyl bromide (0.60 g, 5.5 mmol) were added to magnesium turnings (1.20 g, 49.4 mg atom) in 100 mL of dry THF in a 520 mL round bottom flask equipped with a reflux condenser and magnetic stirrer. The mixture was refluxed with stirring under a static nitrogen atmosphere for 1 h. The reaction mixture was cooled to 0° C. and 7a (6.90 g, 48.5 mmol) in 25 mL of dry THF at 0° C. was added. The mixture was stirred at ambient temp for 1 h and poured into 100 g of ice and 25 ml of 6M HCl. The organic layer was extracted into ether and the ether was washed with water and brine and dried over $MgSO_4$. The ether was evaporated and the byproducts distilled bulb to bulb (120° C./1 torr) to leave 9.8 g (30.4 mmol, 79%) of 8 as a residual oil: IR 3440 (alcohol), 1722 (ester), 1655 (alkene) $cm^{-1}$; $^1H$ NMR δ 1.31 (t, J=7.1 Hz, 3 H), 1.37 (d, J=7.0 Hz, 6 H), 1.99 (s, 3 H), 3.40 (br s, 1 H), 3.75 –3.85 (m, 1 H), 3.847 (s, 3 H), 3.853 (s, 3 H), 4.19 (q, J+7.1 Hz, 2 H), 5.39 (s, 1H), 6.26 (s, 1 H), 6.75 (d, J=8.6 Hz, 1 H), 6.94 (d, J=7.1 Hz, 1 H). Anal. ($C_{18}H_{26}O_5$) C,H.

4-Hydroxy-4-|3,4-dimethoxy-2-(1-methylethyl)phenyl|-3-methylbut-2-enoic Acid (9). Compound 8 (9.00 g, 27.9 mmol) was dissolved in 100 mL of ethanol with 3 g of KOH and refluxed for 1 h. The mixture was poured onto 100 g of ice with 25 ml of 6M HCL and stirred for 24 h. The white solid was filtered, washed with water, dried and recrystallized from ether/petroleum ether to give 7.38 g (25.1 mmol, 90%) of 9 as white plates: mp 154°–155° C.; IR 3411 (OH), 1694 (carbonyl), 1644 (alkene) $cm^{-1}$; $^1H$ NMR δ 1.38 (d, J=7.0 Hz, 6 H), 2.00 (s, 3 H), 3.44 (br s, 1 H), 3.85 (s, 6 H), 5.41 (s, 1H), 6.33 (s, 1 H), 6.75 (d, J=8.6 Hz, 1 H), 6.92 (d, J=7.1 Hz, 1 H). Anal. ($C_6H_{22}O_5$) C,H.

4-|3,4-Dimethoxy-2-(1-methylethyl)phenyl|-3-methylbutanoic Acid (10). Compound 9 (7.00 g, 23.8 mmol) in 100 mL of acetic acid was hydrogenated on a Parr hydrogenator with 0.4 g of 10% palladium on carbon and 60 psi hydrogen pressure at 60° C. for 20 h. The reaction mixture was vacuum filtered through celite and the celite was washed with ether. The solvent was evaporated in a fume hood and the residual oil was distilled bulb to bulb (170° C./1 torr) to give 5.95 g (21.2 mmol, 89%) of 10 as an amber oil which crystallized on standing to form nearly colorless microcrystals: mp 100°–101° C. (lit[14] mp not reported); IR: 1710 (carbonyl) $cm^{-1}$; $^1H$ NMR δ 0.982 (d, J=6.1 Hz, 3 H), 1.33 (d, J=7.1 Hz, 6 H), 2.0–2.7 (m, 5 H), 3.14 (sept, J=7.1 Hz, 1 H), 3.82 (s, 3 H), 3.85 (s, 3 H), 6.62 (d, J=8.0 Hz, 1 H), 6.75 (d, J=8.0 Hz, 1 H). Anal. ($C_{16}H_{24}O_4$) C,H.

6,7-Dimethoxy-3-methyl-5-1(1-methylethyl)-1-oxo-1,2,3,4-tetrahydronaphthalene (11). Compound 10 (5.90 g, 21.0 mmol) was added to 6 g of polyphosphoric ester (Chem. Pharm. Bull. 13: 1065–1072, 1965)in 15 mL of dichloromethane and the mixture was refluxed for 1 h. The reaction mixture was poured over ice, stirred to hydrolyze the polyphosphoric ester and extracted with ether. The ether was evaporated and the residue crystallized from a concentrated methanol solution to give 4.43 g (16.9 mmol, 80%) of 11 as white plates: mp 99°–100° C. (Lit[5] 98°–99° C.); IR 1680 (ketone) $cm^{-1}$; 1H NMR δ 1.16 (d, J=6.1 Hz, 3 H), 1.34 (d, J=7.0 Hz, 6 H), 2.1–3.1 (m, 5 H), 3.35 (sept, J=7.0 Hz, 1 H), 3.885 (s, 3 H), 3.895 (s, 3 H), 7.52 (s, 1 H). Anal. ($C_{16}H_{22}O_3$) C,H.

6,7-dimethoxy-3-methyl-5-(1-methylethyl)-3,4-dihydronaphthalene (12). Compound 11 (4.00 g, 15.2 mmol) was dissolved in 20 mL of isopropanol. $NaBH_4$ (0.57 g, 15 mmol) was added and the reaction mixture was stirred and refluxed for 1 h. It was then cooled and acidified by the dropwise addition of 6M HCl with stirring. The acidified mixture was refluxed for 1 h and then poured onto ice and extracted with ether. The ether layer was washed with water and brine and drived over MgSO$_4$. Petroleum ether was added, the solution was concentrated to remove most of the ether and the product crystallized to give 3.40 g (13.8 mmol, 91%) of 12 as colorless prisms: mp 56°–57° C.; $^1$H NMR δ 1.10 (d, J=7 Hz, 3 H), 1.34 (d, J=7 Hz, 6 H), 2.46 (m, 2 H), 2.92 (m, 1 H), 3.49 (m, 1 H), 3.80 (s, 3 H), 3.83 (s, 3H), 5.81 (m, 1 H), 6.31 (m, 1 H), 6.50 (s, 1 H). Anal. (C$_{16}$H$_{22}$O$_2$) C, H.

2-Bromo-6,7-dimethoxy-3-methyl-5-(1-methylethyl)-3, 4-dihydronaphthalene (13). Compound 12 (3.00 g, 12.2 mmol) was dissolved in 20 mL of dichloromethane and bromine (1.95 g, 12.2 mmol) in 5 ml of dichloromethane was added dropwise with stirring over a period of 15 min. The solvent was evaporation and the residue was taken up in 15 ml of DMF. The DMF solution was warmed to 50°–60° C. for 1 h. The reaction mixture was poured onto ice and stirred. The solid product was filtered, dried and recrystallized from a concentrated petroleum ether solution to give 3.60 g (11.1 mmol, 91%) of 13 as nearly colorless microcrystalline plates: mp 71°–72° C.; $^1$H NMR 1.09 (d, J=6.95, 3 H) , 1.32 (d, J=7.2 Hz, 6 H), 2.4–3.2 (m, 3 H), 3.49 (m, 1 H), 3.80 (s, 3 H), 3.82 (s, 3H), 6.43 (s, 1 H), 6.64 (s, 1H). Anal. (C$_{16}$H$_{21}$BrO$_2$) C, H.

7-Bromo-2,3-dimethoxy-6-methyl-4-(1-methylethyl) naphthalene (14). Compound 13 (3.50 g, 10.8 mmol) was dissolved in 25 mL of benzene and 2,3-dichloro-5,6-dicyano-1,4-benzoquinone (2.45 g, 10.8 mmol) was added slowly with stirring and stirring was continued for 2 h. The reaction mixture was filtered through a short column of silica and eluted with dichloromethane. The solvent was evaporated and the product was crystallized from petroleum ether to give 3.21 g (9.93 mmol, 92%) of 14 as colorless crystals: mp 62°–63° C.; $^1$H NMR δ 1.51 (d, J=7.2 Hz, 6 H), 2.56 (s, 3 H), 3.90 (s, 3 H), 3.96 (s, 3H), 3.97 (m, 1 H), 6.94 (s, 1 H), 7.92 (s, 1 H), 7.96 (s, 1 H). Anal. (C$_{16}$H$_{19}$BrO$_2$) C,H.

6,6',7,7'-Tetramethoxy-3,3'-dimethyl-5,5'-bis(1-methylethyl)-2,2'-binaphthalene (15). Compound 14 (3.00 g, 9.28 mmol) in 25 mL of dry ether was cooled to 0° C. under nitrogen. n-Butyllithium (9.50 mmol) was added as a solution in hexane. The mixture was stirred for 15 minutes at 0° and then finely powdered CoCl$_2$ (1.23 g, 9.50 mmol) and bromobenzene (1.46 g, 9.30 mmol) were added. The mixture was stirred at ambient temp under nitrogen for 24 h. Dichloromethane (100 mL) was added and the organic layer was washed with water and brine. Methanol (100 mL) was added and the mixture was concentrated to incipient crystallization and allowed to cool. Three crops of 15 weighing 1.23 g (2.53 mmol, 53%) total were obtained as a white microcrystalline powder: mp 215°–216° C.; $^1$H NMR δ 1.57 (d, J=7.2 Hz, 12 H), 2.22 (s, 6 H), 3.91 (s, 6 H), 3.95 (s, 6H), 3.95 (m, 2 H), 7.01 (s, 2 H), 7.51 (s, 2 H), 8.00 (s, 2 H). Anal. (C$_{32}$H$_{38}$O$_4$) C,H.

1,1'-Bisdeoxygossypol Tetramethyl Ether (16; 6,6',7,7'-Tetramethoxy-3,3'-dimethyl-5,5'-bis(1-methylethyl) |2,2'-binaphthalene|-8,8'-dicarboxyaldehyde). A reaction mixture consisting of 15 (1.10 g, 2.26 mmol) and dichloromethyl methyl ether (1.30 g, 11.3 mmol) in 50 mL of dry dichloromethane under nitrogen was cooled in an ice bath. Titanium tetrachloride (1.20 g, 6.33 mmol) was added dropwise with stirring. The mixture was allowed to come to ambient temp and was stirred for 2 h. The reaction mixture was poured onto 100 g of ice with 10 mL of 6 M HCl and stirred. The mixture was extracted with methylene chloride and the organic layer was washed with water and brine and drived over magnesium sulfate. The solvent was evaporated and the product was crystallized from acetone to give 1.02 g (1.89 mmol, 84%) of light yellow 16 as microcrystalline prisms: mp 269°–270° C.; IR 1675 (aldehyde) cm$^{-1}$; $^1$H NMR δ 1.53 (d, J=7.2 Hz, 12 H), 2.20 (s, 6 H), 3.90 (s, 6 H), 3.99 (s, 6H), 4.03 (m, 2 H), 8.02 (s, 2 H), 9.01 (s, 2 H), 10.68 (s, 2 H). Anal. (C$_{34}$H$_{38}$O$_6$) C.H.

1,1'-Bisdeoxygossypol (3; 6,6',7,7'-Tetrahydroxy-3,3'-dimethyl-5,5'-bis(1-methylethyl) |2,2'-binaphthalene|-8,8'-dicarboxaldehyde). Compound 16 (0.500 g, 0.921 mmol) in 15 mL of dichloromethane under nitrogen was cooled to −79°. Boron tribomide (450 μL, 4.74 mmol) was added with stirring and the mixture was stirred at −79° for 1 h. Stirring was continued at 0° C. for 1 h and at ambient temp for 1 h. The reaction mixture was cooled on in an ice bath and then ice and a few drops of dilute HCl were added with stirring. The mixture was extracted with ether and the ether layer was washed with water and brine and dried over magnesium sulfate. Petroleum ether was added and the solution was concentrated and the product allowed to crystallize to give 0.370 g (0.760 mmol, 83%) of 3 as a light brown microcrystalline powder: mp 269°–270° C.; IR 3540, 3320 (phenols), 1630 (aldehyde) cm$^{-1}$; $^1$H NMR δ 1.56 (d, J=7.0 Hz, 12 H), 2.25 (s, 6 H), 3.96 (sept, J=7.0 Hz, 2 H), 6.22 (s, 2H), 8.05 (s, 2H), 8.13 (s, 2H), 10.64 (s, 2 H), 13.78 (s, 2 H). Anal. (C$_{30}$H3\$_{30}$O$_6$) C,H.

1,1'-Bisdeoxygossylic Acid Tetramethyl Ether (17; 6,6', 7,7'-Tetramethoxy-3,3'-dimethyl-5,5'-bis(1-methylethyl) |2,2'-binaphthalene|-8,8'-dicarboxylic Acid. Finely powdered 16 (0.500 g, 0.921 mmol) as a slurry in 20 mL of acetonitrile was cooled in an ice bath and 60 mg of NaH$_2$PO$_4$ and 200 μL of 30% H$_2$O$_2$ were added. Then 0.287 g (3.17 mmol) of sodium chlorite dissolved in 2 mL of water was added. The reaction mixture was stirred at ambient temp for 24 h and then poured onto 40 g of ice with 10 mL of 6M HCl. The produce was filtered off, taken up in 10 ml of acetone and chilled. The acetone solution was filtered to remove insoluble byproducts. Ether and petroleum ether were added and the solution was concentrated to incipient crystallization. The first crop of cream colored 17, in the form of microcrystalline plates, weighed 0.455 g (0.792 mmol, 86%): mp 258°–259° C.; IR 1695 (carbonyl); $^1$H NMR δ 1.55 (d, J=7.1 Hz, 12 H), 2.45 (s, 6 H), 3.91 (s, 6H), 3.95 (buried sept), 4.00 (s, 6H), 8.04 (s, 2 H), 8.11 (s, 2 H). Anal. (C$_{34}$H$_{38}$O$_8$) C,H.

1,1'Bisdeoxygossylic Acid (4; 6,6',7,7'-Tetrahydroxy-3,3'-dimethyl-5,5'-bis(1-methylethyl) |2,2'-binaphthalene|-8,8'-dicarboxylic Acid. Compound 17 (0.400 g, 0.696 mmol) in 15 mL of dichloromethane under nitrogen was cooled to −79°. Boron tribromide (460 μL, 1.22 g, 4.87 mmol) was added with stirring and the mixture was stirred at −79° C. for 1 h. at 0° C. for 1 h and at ambient temp for 1 h. The reaction mixture was cooled on ice and then 15 mL of ice water with a few drops of HCl were added with stirring. The mixture was extracted with ether and the ether layer was washed with water and brine and dried over magnesium sulfate. The solvent was evaporated and the product was recrystallized from ether/petroleum ether to give 260 mg (0.501 mmol, 72%) of brown 4 as a microcrystalline powder: decomposes above 225° C.; IR 3545 (phenol), 1640 (carbonyl) cm$^{-1}$; $^1$H NMR δ 2.25 (d, J=7.2 Hz, 12 H), 2.26 (s, 6 H), 3.95 (sept, J=7.2 Hz, 2 H), 6.28 (br s, 2 H), 7.45 (br s, 2H), 8.02 (s, 2 H), 8.63 (s, 2 H). Anal. (C$_{30}$H$_{30}$O$_8$) C, H.

2,3-Dimethoxy-6-methyl-4-(1-methylethyl)naphthalene (18). Compound 12 (3.00 g, 12.2 mmol) was dissolved in 25 mL of benzene and 2,3-dichloro-5,6-dicyano-1,4-benzoquinone (2.80 g, 12.2 mmol) was added slowly with stirring and stirring was continued for 3 h. The reaction mixture was filtered through a short column of alumina which was washed with dichloromethane. The solvent was evaporated from the colorless eluant and the residual product was crystallized from petroleum ether to give 2.83 g (11.6 mmol, 95%) of 18 as colorless microcrystalline plates: mp 62°–63° C.; $^1$H NMR: δ 1.51 (d, J=7.2 Hz, 6 H), 2.50 (s, 3 H), 3.88 (s, 3 H), 3.90 (sept, J=7.2 Hz, 1 H), 3.94 (s, 3 H), 7.01 (s, 1 H), 7.20 (d, J=8.3 Hz, 1 H), 7.60 (d, J=8.3 Hz, 1 H), 7.88 (s, 1 H). Anal. ($C_{16}H_{20}O_2$) C, H.

8-Deoxyhemigossypol dimethyl ether (19; 2,3-dimethoxy-6-methyl-4-(1-methylethyl)-1-naphthaldehyde. A reaction mixture consisting of 18 (2.5 g, 10.2 mmol) and dichloromethyl methyl ether (3 g, 2.4 ml, 26.5 mmol) in 20 mL of dichloromethane under nitrogen was cooled in an ice bath. Titanium tetrachloride (1.5 ml, 14 mmol) was added slowly with stirring. The mixture was stirred into 100 g of ice with 10 mL of 6M HCl and the reaction mixture was extracted with ether. The ether layer was washed with water and brine and dried over magnesium sulfate. Petroleum ether was added, the solution was concentrated and the product was allowed to crystallize to give 2.28 g (8.36 mmol, 82%) of 19 as light yellow crystals: mp 103°–104° C.; IR 16865 (aldehyde); $^1$H NMR δ 1.52 (d, J=7.2 Hz, 6 H), 2.50 (s, 3 H), 3.91 (s, 3 H), 3.99 (sept, J=7.2 Hz, 1 H), 4.02 (s, 3 H), 7.38 (d, J=8.7 Hz, 1 H), 7.93 (br s, 1 H), 9.16 (d, J=8.7 Hz, 1 H), 10.75 (s, 1 H). Anal. ($C_{17}H_{20}O_3$) C,H.

8-Deoxyhemigossypol (5; 2,3-dihydroxy-6-methyl-4-(1-methylethyl)-1-naphthaldehyde. Compound 19 (1 g, 3.7 mmol) in 10 mL of dichloromethane was cooled to –79° under nitrogen. Boron tribromide (2 g, 755 µL, 8 mmol) was added with stirring and the mixture was stirred under nitrogen at –79° for 1 h, at 0° C. for 1 h and at ambient temp for 1 h. The reaction mixture was cooled on ice and 10 mL of ice water with few drops of HCl were added with stirring. The mixture was extracted with ether and the ether layer washed with water and brine and dried over magnesium sulfate. The ether was evaporated and the product recrystallized from methanol to give 5 (0.65 g, 72%) as fine, gold colored needles: mp 170°–171° C.; IR 3520 (phenol), 1640 (aldehyde) cm$^{-1}$; $^1$H NMR δ 1.47 (d, J=7.2 Hz, 6 H), 2.47 (s, 3 H), 3.85 (sept, J=7.2 Hz, 1 H), 6.13 (s, 1 H), 7.27 (d, J=8.6 Hz, 1 H), 7.86 (br s, 1 H), 8.15 (d, J=8.6 Hz, 1 H), 10.65 (s, 1 H), 13.64 (s, 1 H). Anal. ($C_{15}H_{16}O_3$) C.H.

8-Deoxyhemigossylic Acid Dimethyl Ether (20; 2,3-dimethoxy-6-methyl-4-(1-methylethyl)-1-naphthoic acid. Compound 19 (1.0 g, 3.67 mmol) in 25 mL of acetonitrile was cooled in an ice bath and 120 mg of $NaH_2PO_4$ and 400 µL of 30% $H_2O_2$ were added. Then sodium chlorite (0.500 g, 5.53 mmol) dissolved in 5 mL of water was added. The reaction mixture was stirred at ambient temp for 2 h and then poured onto 100 g of ice with 10 mL of 6M HCl and extracted with ether. The ether layer was washed with water and brine and dried over magnesium sulfate. The solvent was allowed to evaporate and the residual solid was crystallized from petroleum ether to give 0.889 g (3.08 mmol, 84%) of light yellow 20 as a microcrystalline powder: mp 159°–160° C.; IR 3210 (—OH), 1730 (carbonyl) ch$^{-1}$; $^1$H NMR δ 1.53 (d, J=7.2 Hz, 6 H), 2.53 (s, 3 H), 3.94 (s, 3H), 3.95 (buried sept), 4.05 (s, 3 H), 7.37 (d, J=8.7 Hz, 1 H), 7.95 (s, 1 H), 8.19 (d, J=8.7 Hz, 1 H), 11.0 (br s, 1 H). Anal. ($C_{17}H_{20}O_4$) C.H.

8-Deoxyhemigossylic Acid (6; 2,3-dihydroxy-6-methyl-4-(1-methylethyl)-1-naphthoic Acid. Compound 20 (0.500 g, 1.73 mmol) in 15 mL of dichloromethane under nitrogen was cooled to –79° C. Boron tribromide (0.640 mL, 1.69 g, 6.75 mmol) was added with stirring and the mixture was stirred under nitrogen at –79° for 1 h, at 0° C. for 1 h and at ambient temp for 1 h. The reaction mixture was cooled on ice and 15 mL of ice water with few drops of HCl were added with stirring. The mixture was extracted with ether and the ether layer washed with water and brine and dried over magnesium sulfate. The solvent was evaporated and the product was recrystallized from ether/petroleum ether to give 0.284 g (1.09 mmol, 63%) of brown 6 as microcrystalline needles: mp 173°–174° C. decomp; IR 3540 (phenol), 1630 (carbonyl) cm$^{-1}$; $^1$H NMR δ 1.52 (d, J=7.0 Hz, 6 H), 2.51 (s, 3 H), 3.91 (sept, J=7.0 Hz, 1 H), 6.29 (s, 1 H), 7.31 (d, J=8.9 Hz, 1 H), 7.91 (s, 1 H), 8.74 (d, J=8.9 Hz, 1 H), 12.8 (s, 1H). Anal. ($C_{15}H_{16}O_4$) C,H.

Example II. Anti-HIV Testing

The anti-HIV assay used was based on a published procedure (*J. Virol.* 62:3779–3788, 1988) using HT46c (HeLaT4+) cells as host cells for the H9/HIV-III$_B$ strain of the HIV-1 virus. The cells were seeded into 6-well plates, $5 \times 10^4$ cells/well, in RPMI 1640 with 10% FBS and allowed to attach overnight. After treatment of the wells with DEAE-dextran, stock virus was added at a concentration that produces 100–200 foci/well on day 3 in positive control wells. Test compounds were added, and plates incubated for 3 days at 37° C., 5% $CO_2$. Monolayers were fixed with methanol and wells analyzed with a focal immunoassay (FIA). The primary reagent used in the FIA was a polyclonal antibody preparation of sera from AIDS patients. The secondary reagent was a goat anti-human IgG antibody tagged with horseradish peroxidase. The substrate was 3-amino-9-ethylcarbazole in sodium acetate buffer with hydrogen peroxide. Each compound was tested at concentrations of 0.01, 0.1, 1.0, 5.0 and 20 µM. GIL was tested as a standard for comparison.

Example III. Fluorescence Quenching Titrations

These experiments were carried out at 25° C. in 2 mL volumes of 0.2M potassium phosphate buffer (pH 7.4) containing 0.1M sodium chloride. Aliquots of a 1 mM stock solution of test compound in DMSO were added to a 10 µM solution of human serum albumin in the buffer. Fluorescence was measured with a Perkin Elmer model LS 50 luminescence spectrometer. The Kds were determined by plotting the reciprocal of free ligand concentration versus the reciprocal of fractional quenching. This plot provides –1/Kd as the x-intercept. Details of the calculations employed are set forth in *J. Pharm. Sci.* 77:237–240 (1988).

The products and intermediates of the inventions are illustrated in the reaction schemes and examples in terms of specific compounds selected for their convenience and/or particular effectiveness in the practice of the inventions. However, the methyl and isopropyl groups of the illustrated compounds may also be hydrogen or alkyl groups such as other substituted or unsubstituted $C_1$–$C_4$-alkyl groups as set forth in the claims. The illustrated methoxy and butenoate substituents may also comprise other alkyl substituents such as other substituted or unsubstituted $C_1$–$C_4$-alkoxy groups or substituted or unsubstituted $C_1$–$C_4$-alkenoates, respectively. As known in the art, such other selected substituents should not substantially adversely affect the desired properties of the compounds as compared to the illustrated compounds, particularly the reactivities of the reagents and/or the biological properties of the biologically active compounds such as the compounds of claim 1. Further, the halo group employed in form the Grignard reagent and in the coupling reaction may be other than bromo, with the same caveats.

What is claimed is:

1. A compound of the formula:

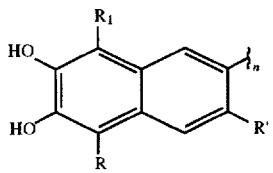

wherein R and R' are independently H or substituted or unsubstituted $C_1$-$C_4$-alkyl; $R_1$ is

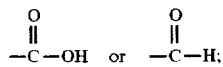

and n is 2.

2. A compound according to claim 1, wherein $R_1$ is

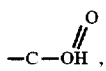

n is 2, and R and $R^1$ are independently substituted or unsubstituted $C_1$-$C_4$-alkyl.

3. A compound according to claim 1, wherein $R_1$ is

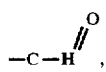

n is 2, and R and $R^1$ are independently substituted or unsubstituted $C_1$-$C_4$-alkyl.

4. A compound of the formula:

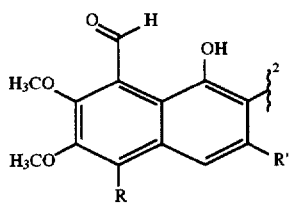

wherein R and R' are independently H or substituted or unsubstituted $C_1$-$C_4$-alkyl.

5. A compound according to claim 2, wherein R is isopropyl and R' is methyl.

6. A compound according to claim 3, wherein R is isopropyl and R' is methyl.

7. A compound according to claim 4, wherein R is isopropyl and R' is methyl.

8. A method for preparing a compound according to claim 4, comprising:

a) converting a halodimethoxy benzene of the formula:

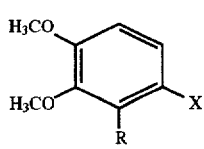

to a Grignard reagent and reacting the reagent with an oxobutenoate of the formula:

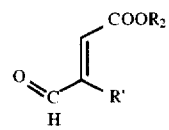

to form a 4,4-hydroxyphenylbutenoate of the formula:

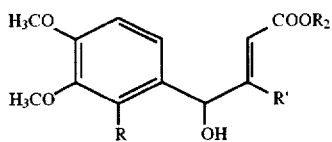

b) saponifying the ester product of the Grignard reaction to the corresponding butanoic acid and catalytically hydrogenolyzing and reducing the acid to form a 4-phenylbutanoic acid of the formula:

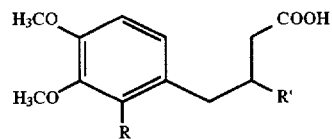

c) cyclizing the 4-phenylbutanoic acid to a tetrahydronaphthalene of the formula:

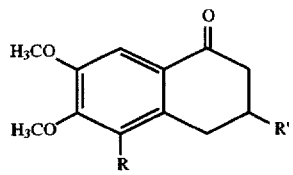

and reducing and rehydrating the product to the corresponding dihydronaphthalene of the formula:

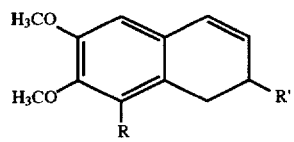

d) wherein in the above formulas R and R' are independently H or substituted or unsubstituted $C_1$-$C_4$-alkyl, $R_2$ is $C_1$-$C_4$-alkyl, and X is halo.

9. The method of claim 8, wherein the butanoic acid of step (b) is catalytically hydrogenolyzed and reduced in a one step reaction.

10. The method of claim 9, wherein the 4-phenylbutenoic acid of claim 3 is cyclized with a polyphosphoric ester.

11. A method for preparing a 1,1-bisdeoxygossypol ether according to claim 4 comprising:

a) halogenating and dehydrogenating the dihydronaphthalene of the formula:

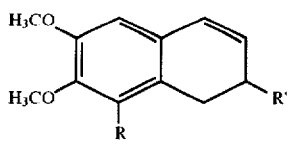

to produce a halogenated naphthalene monomer of the formula:

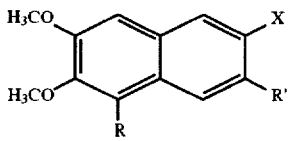

b) coupling two of the monomers to form a corresponding dimer of the formula:

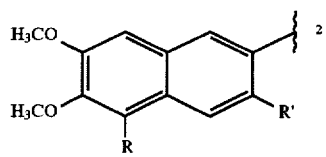

and c) formylating the dimer to:

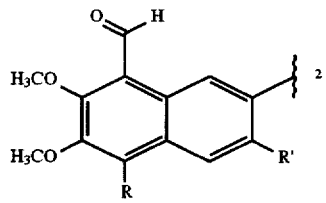

d) wherein R and R' are independently H or substituted or unsubstituted $C_1$–$C_4$-alkyl, and X is halo.

12. The method of claim 11, wherein the monomers are coupled in step (b) by lithiating with a $C_2$–$C_4$-alkyl lithium compound and coupling in the presence of a cobalt halide catalyst.

13. The method of claim 12, wherein the lithium compound is n-butyllithium, and the catalyst is cobalt chloride.

14. A method for preparing a 1'1-bisdeoxygossypol of the formula:

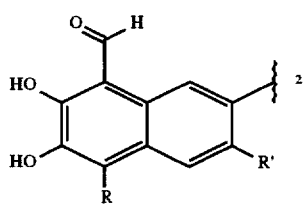

comprising demethylating the dimer product of claim 11.

15. A method for preparing a 1'.1-bisdeoxygossylic acid of the formula:

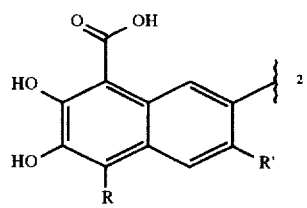

comprising oxidizing and demethylating the dimer product of claim 11.

16. A method for preparing an 8-deoxyhemigossypol ether of the formula:

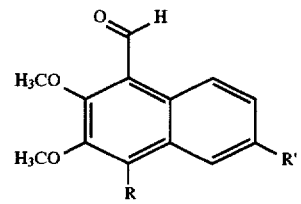

comprising dehydrogenating and formylating the dihydronaphthalene product of claim 8.

17. A method for preparing an 8-deoxyhemigossylic acid of the formula:

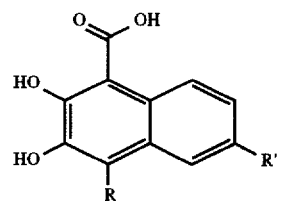

comprising oxidizing and demethylating the ether product of claim 16.

18. A method for preparing an 8-deoxyhemigossypol of the formula:

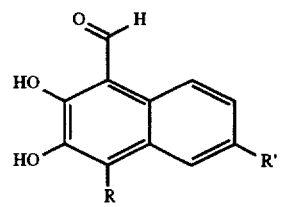

comprising demethylating the ether product of claim 16.

19. The method of claim 8, wherein X is bromo.

20. The method of claim 11, wherein X is bromo.

21. A method for treating an enveloped virus infection in a mammal comprising administering a compound according to one of claims 1, 2, 3, 5 or 6 the mammal in a pharmaceutically effective amount.

22. A pharmaceutical composition comprising a compound according to one of claims 1, 2 or 3 and a pharmaceutically-acceptable carrier.

23. A dimer of the formula:

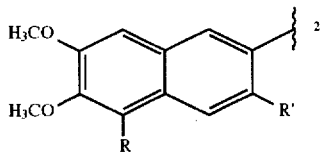

wherein R and R' are independently H or substituted or unsubstituted $C_1$–$C_4$-alkyl.

24. A method for preparing a dimer according to claim 23, comprising halogenating 6,7-dimethoxy-3-R'-(R)-3,4-dihydronaphthalene to its corresponding 2-halo derivative; dehydrogenating this derivative to the corresponding 7-halo-2,3-dimethoxy-y-R'-4-(R)-naphthalene monomer, and coupling two of the monomers to form the dimer, wherein R and R' are as defined in claim 23.

25. The method of claim 24, wherein halogenating is brominating and halo is bromo.

26. The method of claim 24, wherein the monomers are coupled by lithiating with a $C_1$–$C_4$-alkyl lithium compound and coupled in the presence of a cobalt halide catalyst.

27. The method of claim 26, wherein the lithium compound is n-butyllithium and the catalyst is cobalt chloride.

28. The method of claim 25, wherein R' is methyl and R is isopropyl.

* * * * *